United States Patent [19]

Aslam et al.

[11] Patent Number: 5,041,614

[45] Date of Patent: Aug. 20, 1991

[54] METHOD FOR THE PREPARATION OF 4-ACETOXYSTYRENE

[75] Inventors: Mohammad Aslam; Charles B. Hilton, both of Corpus Christi, Tex.

[73] Assignee: Hoechst Celanese Corporation, Somerville, N.J.

[21] Appl. No.: 548,170

[22] Filed: Jul. 3, 1990

[51] Int. Cl.$^5$ ............................................. C07C 67/297
[52] U.S. Cl. ..................................... 560/130; 526/75; 560/239
[58] Field of Search ................................ 560/130, 239

[56] References Cited

U.S. PATENT DOCUMENTS 4,927,956  5/1990  Vicari et al. ........................ 560/130

OTHER PUBLICATIONS

Corson et al., *J. Org. Chem.*, vol. 23, (1958).
Arshady et al., *J. Poly. Sci.*, vol. 12, 2017–2025, (1974).

*Primary Examiner*—Jose G. Dees
*Assistant Examiner*—Vera C. Clarke
*Attorney, Agent, or Firm*—Jerome Rosenstock; Shirley L. Church

[57] ABSTRACT

A method for the preparation of 4-acetoxystyrene is disclosed. The method comprises heating 4'-acetoxyphenylmethylcarbinol in the presence of a suitable acid anhydride and a suitable dehydration catalyst in a continuous feed reaction mode to make the 4-acetoxystyrene.

32 Claims, No Drawings

METHOD FOR THE PREPARATION OF 4-ACETOXYSTYRENE

BACKGROUND OF THE INVENTION

1. Field of the Invention

This invention relates to a method for the preparation of 4-acetoxystyrene, and more particularly for the preparation of 4-acetoxystyrene by heating in a continuous feed reaction mode 4'-acetoxyphenylmethylcarbinol in the presence of a suitable acid anhydride and a suitable dehydration catalyst.

2. Description of the Prior Art

4-Acetoxystyrene is a well-known compound which is useful as an intermediate in the preparation of compounds useful in the production of adhesives, photoresists, etc. The preparation of 4-acetoxystyrene is well-known in the art, however a more efficient process for preparing 4-acetoxystyrene whereby increased yields and increased reaction selectivity (where selectivity is the ratio of the yield of 4-acetoxystyrene to conversion of 4'-acetoxyphenylmethylcarbinol) is desired and needed. The instant invention provides a method whereby such increased yields and selectivity is obtained.

SUMMARY OF THE INVENTION

The present invention is directed to a method for the preparation of 4-acetoxystyrene and more particularly, for the preparation of 4-acetoxystyrene by heating in a continuous feed reaction mode 4'-acetoxyphenylmethylcarbinol in the presence of a suitable acid anhydride and a suitable dehydration catalyst.

DETAILED DESCRIPTION

The present invention relates to a method of synthesizing 4-acetoxystyrene of the formula

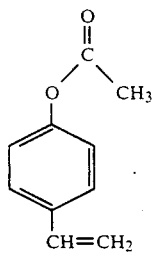

(I)

The synthesis of Compound I is made in the following manner. 4'-Acetoxyphenylmethylcarbinol of the formula

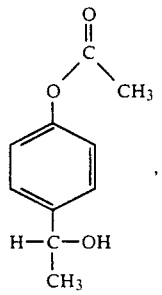

(II)

a known compound, which may be synthesized in accordance with the teachings of Carson et al. *J. Org. Chem.* 23,544 (1958), is selected. Compound II is combined with a suitable acid anhydride, of the formula

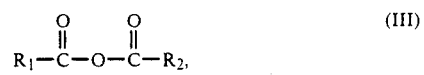

(III)

and Compound II is then subjected to dehydration, as by heating, in a continuous feed reaction mode. The heating or dehydration, e.g. dehydration by conventional vacuum dehydration, is conducted in the presence of a suitable dehydration catalyst and, optionally, a conventional polymerizing inhibitor, which inhibits the polymerization of the resultant 4-acetoxystyrene monomer to a polymer, to form Compound I and $H_2O$ as a by-product.

It is critical that the heating or dehydration be carried out both in the presence of a suitable acid anhydride and via a continuous or semi-continuous feed reaction mode. If the acid anhydride is not employed, the water (by-product) which is formed during the dehydration reacts with Compound I and starting materials to yield undesireable by-products and ultimately leading to an undesired amount of a polymer residue. Thus, the acid anhydride acts as a water scavenger by reacting therewith to form an acid and thereby reduces or controls the amount of undesired polymer residue. In addition, the continuous or semi-continuous feed reaction mode permits rapid and continuous removal of both Compound I and a co-product, where the co-product can be unreacted water, or resultant acid or a mixture of water and acid, whereby the amount of polymer residue is controlled.

A suitable acid anhydride, Compound III, is one where $R_1$ and $R_2$ are independently lower alkyl or aryl, where the term "lower" means the group it is describing contains from 1 to 10 carbon atoms; the term "alkyl" refers to a straight or branched chain hydrocarbon containing no unsaturation, e.g. methyl, ethyl, isopropyl, 2-butyl, n-pentyl, n-hexyl, etc; the term "aryl" refers to a monovalent substituent which consists of an aryl group, e.g. phenyl, o-toluyl, m-trifluoromethyl phenyl, etc., of the formula

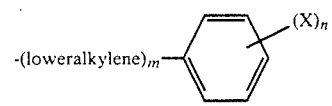

where X is hydrogen, loweralkyl, $CF_3$, $NO_2$, $NH_2$, and n is an integer of 1 to 5, m is an integer of 0 or 1 and where the term "alkylene" refers to a bivalent radical of the lower branched or unbranched alkyl group it is derived from having valence bonds from two terminal carbons thereof, e.g. ethylene ($-CH_2CH_2-$), propylene ($-CH_2CH_2CH_2-$), isopropylene

etc.

A suitable dehydration catalyst includes any conventional dehydrating catalyst such as a mineral acid catalyst, e.g. $H_2SO_4$, HCl, phosphoric acid, polyphosphoric acid, etc.; an ion exchange acidic resin, e.g. Amberlyst ®, Nafion-H ®, etc.; an organic acid, e.g. p-toluenesulfonic acid, methanesulfonic acid, etc.; and inorganic oxides, e.g. alumina, titania, silica gel, etc. or any suitable mixture thereof. Preferred dehydration catalysts are inorganic bisulfate salts such as ammonium bisulfate, potassium bisulfate and acids such as phosphorous acid, phosphoric acid and p-toluenesulfonic acid. A most preferred catalyst is phosphoric acid.

The polymerization inhibitors include t-butyl catechol, hydroquinone, tetrachloroquinone, phenothiazine and di-t-butyl-p-cresol.

The preferred concentration of the suitable anhydride, Compound III is slightly in excess of a 1 to 1 molar ratio to Compound II, typically ranging from about 0.25 to about 1.25. The dehydration catalyst is present in the dehydration reaction mixture in an amount which results in the greatest yield of Compound I and will vary with the particular dehydration catalyst employed. Such a concentration is one which can be easily obtained by one of ordinary skilled in the art in view of the disclosure contained herein without an undue amount of experimentation. For example, based upon the moles of Compound II present, typically the concentration of ammonium bisulfate ranges from about 0.30 mole percent to about 0.50 mole percent; for phosphorous acid typically from about 0.40 mole percent to about 0.60 mole percent; for 85 weight percent phosphoric acid typically from about 0.25 mole percent to about 0.40 mole percent; and for p-toluenesulfonic acid typically from about 0.20 mole percent to about 0.35 mole percent.

The concentration of the polymerization inhibitor is not critical and it is typically present in an amount ranging from about 0.01 weight percent to about 1.0 weight percent based on the weight of Compound II.

The reaction may be carried out in a reaction system comprising a reaction vessel pre-heated to above the boiling point of 4-acetoxystyrene at the operating pressure, which is destined to receive a reaction mixture comprising Compound II, Compound III, the dehydration catalyst and the polymerization inhibitor. The reaction vessel is connected via an exit conduit to a condensor. A vacuum source is typically connected to a vapor outlet from the condensor, or a receiver attached to the condensor. It is to be understood that any other conventional dehydration reaction apparatus can be employed. For example, the dehydration or heating can be carried out in a low residence thin film evaporator, the output of which connects to a distillation column, where the mixture is constantly mixed by a rotating wiper in the evaporator. The reaction is typically carried out at a temperature of from about 150° C. to about 300° C., preferably about 170° C. to about 250° C., and most preferably at about 180° to about 220° C. The pressure at which the dehydration is conducted ranges from about 5 mmHgA to about 250 mmHgA, preferably about 30 mmHgA to about 150 mmHgA, most preferably about 40 mmHgA to about 100 mmHgA.

Optimally, the reaction of Compound II caused by heating in the presence of Compound III and the aforementioned catalyst and polymerization inhibitor be carried out in a continuous or semi-continuous process mode. By a continuous process is meant the feeding of the reaction mixture and removal of the products of the reaction is accomplished a by continuous flow of feed of reaction mixture and removal of reaction products, at an approximately constant rate, to and from the reaction system, including the reaction vessel and distillation apparatus. By a semi-continuous process is meant the aforementioned continuous process with periods of interruption of the feeding of the reaction mixture, or removal of products, as required to maintain high efficiency and/or yield or operability.

The reaction mixture (comprising Compound II, Compound III, the dehydration catalyst and the polymerization inhibitor) is introduced in a continuous or semi-continuous manner such as by being pumped, as for example by a peristaltic pump, into the aforementioned heated reaction vessel, or thin film evaporator at the requisite temperature, vacuum, as described above, to obtain the target Compound I and the by-product, water. As indicated previously, in the dehydration, water is formed which in turn reacts with the suitable acid anhydride, e.g. acetic anhydride, or is removed in part from the reactor by distillation to form as a by-product an organic acid, e.g. acetic acid, alone or combined with any remaining water. Both the target Compound I and the co-product (water or organic acid alone or water and organic acid) which form are continuously removed from the reaction vessel by distillation through a conventional distillation column joined to the reaction vessel. Compound I and the co-product are condensed and collected in an overhead receiver while unreacted Compound II may or may not be separated from Compound I and co-product in the distillation column. If Compound II is not separated from Compound I and co-product in this step, it is then further separated in a second distillation step. If Compound II is separated in the first distillation column, it is returned to the reaction vessel by return of reflux. The continuous removal of the target Compound I and the co-product is carried out in conjunction with the continuous introduction of feed reaction mixture to the aforementioned reaction vessel.

Since it is desirable to feed the reaction mixture at about the same rate as Compound I and the co-product are removed, removal of Compound I and the co-product introduction of reaction mixture portion can be sequenced by any conventional timing device or sequencer, which controls the pumping mechanism, e.g. peristaltic pump.

It has been found that if the dehydration is carried out in the continuous or semi-continuous feed reaction mode that a good yield of Compound I with high selectivity is obtained.

It has been found that, although a suitable acid anhydride, (Compound III), is provided and even though a continuous or semi-continuous feed reaction mode dehydration is carried out, a certain amount or quantity of polymer residue is produced. If too much of the polymer accumulates in the reaction vessel then the yield of Compound I and the selectivity are adversely affected. On the other hand, it has surprisingly been found that a certain amount of polymer residue in the reaction vessel yields an optimum yield and selectivity. The amount or quantity of polymer residue which yields such optimum results is a desired steady state or a variable state having a lower and upper limit. The steady state is from about 1 percent by volume of the volume of the reaction vessel to about thirty percent by volume of the volume of the reaction vessel. A preferred steady state concentration is from about 5 percent by volume of the volume of the reaction vessel to about 15% by volume of the volume of the reaction vessel.

The variable state has a lower limit of from about 1% to about 29% by volume of the volume of the reaction vessel to an upper limit of from about 2% to about 30% by volume of the volume of the reaction vessel.

The quantity of the polymer residue may be controlled by having a continuous removal of undesired quantities of the residue, as for example by continuously pumping the residue from the reaction vessel at a uniform rate to achieve the desired steady state concentration of the residue, i.e. about 1 to about 30 volume percent, preferably about 5% to about 15% by volume of the volume of the reaction vessel, or a variable desired quantity ranging from the lower limit to the upper limit. This continuous removal takes place as the reactant mixture of Compound II, Compound III, dehydration catalyst and inhibitor, is dehydrated in a continuous or semi-continuous feed reaction mode. Alternatively, the undesired quantity of residue can be removed periodically. In one embodiment, a first portion of reactant mixture is introduced into the reaction vessel in a continuous feed reaction mode to yield a first portion of Compound I and a first portion of polymer residue. Upon exceeding a desired quantity of polymer residue, e.g. about 5 to about 15 percent by volume of the volume of the reaction vessel, the lower limit (about 1 to about 29 volume percent) or upper variable state limit (about 2 to about 30 volume percent), some or all of this first portion of residue is removed, e.g. as by pumping, to yield and maintain a desired quantity of residue. A second portion of reactant mixture is then introduced into the reaction vessel and reacted in the same manner to yield a second portion of Compound I and additional residue. The residue removal-reaction sequence is repeated until all of the reactant mixture desired to be reacted has been reacted in the presence of a maintained, desired range of residue amount or quantity.

Presented below are the results of several experiments which illustrate how the practice of the subject invention leads to better yields of Compound I with a higher selectivity. In this regard, reference is made to Table I which reports the results of several experiments where the dehydration of Compound II was carried out in a 3-necked, 250 ml glass reaction vessel which was immersed in a hot oil bath maintained at the desired temperature. A reaction mixture was contained in a second glass vessel which was connectively joined to the reaction vessel through one neck thereof, by means of a peristaltic pump which had a conventional electrical sequence timer controlling it to affect the continuous reaction mode described above. The peristaltic pump was used to pump the reaction mixture contained in the second glass vessel into the reaction vessel for dehydration and formation of Compound I and co-product. Connected to the reaction vessel through a second neck thereof, was a conventional distillation column through which Compound I and the co-product (acid and unreacted water) were allowed to vaporize from the reaction vessel continuously via an overhead receiver attached to the conventional distillation column. A conventional vacuum pump system was also connected to the interior of the reaction flask to attain the desired vacuum.

In experiments 1 through 19 of Table I, crude Compound II, containing 80-95 percent by weight of Compound II, was combined with acetic anhydride (Ac$_2$O) in the indicated amounts and the inhibitor phenothiazine (0.1 weight percent). The reaction mixture was fed to the reaction vessel which was immersed in hot oil maintained at 220° C. at a rate of about 2.0 g/min, keeping the resultant residue which was formed at a temperature above 180° C.

TABLE I

| Exp. No. | Compound II (Moles Fed) | Ac$_2$O (Moles Fed) | Cat. Used | Cat. (Mole %) | Compound I (Moles) | Compound II (Conv. %) | Compound I Selectivity (%) | Compound I Yield (%) |
|---|---|---|---|---|---|---|---|---|
| 1 | 0.84 | 1.03 | 85% PA | 0.17 | 0.11 | 20.06 | 65.98 | 13.24 |
| 2 | 0.85 | 1.03 | 85% PA | 0.25 | 0.57 | 72.18 | 91.93 | 66.35 |
| 3 | 0.86 | 1.06 | 85% PA | 0.29 | 0.66 | 87.28 | 88.24 | 77.02 |
| 4 | 0.83 | 1.03 | 85% PA | 0.32 | 0.65 | 92.91 | 84.73 | 78.72 |
| 5 | 0.82 | 1.00 | 85% PA | 0.35 | 0.64 | 94.93 | 81.91 | 77.75 |
| 6 | 0.80 | 1.00 | 85% PA | 0.38 | 0.60 | 95.78 | 78.31 | 75.00 |
| 7 | 0.94 | 1.00 | TSA | 0.17 | 0.35 | 45.69 | 80.70 | 36.87 |
| 8 | 0.86 | 1.04 | TSA | 0.24 | 0.65 | 79.47 | 95.38 | 75.79 |
| 9 | 0.83 | 1.00 | TSA | 0.31 | 0.62 | 90.90 | 81.80 | 74.36 |
| 10 | 0.84 | 1.05 | TSA | 0.38 | 0.47 | 91.74 | 60.67 | 55.66 |
| 11 | 0.92 | 1.00 | PA | 0.17 | 0.04 | 11.51 | 41.21 | 4.74 |
| 12 | 0.91 | 1.00 | PA | 0.24 | 0.07 | 19.77 | 36.57 | 7.23 |
| 13 | 0.94 | 1.03 | PA | 0.38 | 0.54 | 71.26 | 80.69 | 57.50 |
| 14 | 0.92 | 1.00 | PA | 0.52 | 0.58 | 79.79 | 78.84 | 62.91 |
| 15 | 0.92 | 1.00 | AB | 0.17 | 0.13 | 41.93 | 34.29 | 14.38 |
| 16 | 0.91 | 1.00 | AB | 0.24 | 0.31 | 62.25 | 54.14 | 33.70 |
| 17 | 0.91 | 1.00 | AB | 0.31 | 0.53 | 75.24 | 76.54 | 57.59 |
| 18 | 0.92 | 1.00 | AB | 0.38 | 0.66 | 85.43 | 84.52 | 72.21 |
| 19 | 0.91 | 0.96 | AB | 0.45 | 0.70 | 86.88 | 87.85 | 76.32 |

85% PA = 85% Phosphoric aicd.
TSA = p-Toluenesulfonic acid.
PA = Phosphorus acid.
AB = Ammonium bisulfate.
Ac$_2$O = Acetic anhydride.

Thus, it can be seen that the proper selection of catalyst, catalyst concentration, etc. will lead to a selectivity of about 95% and a conversion to Compound I from Compound II at about 78%.

The criticality of using an acid anhydride is illustrated in Table II, below, where the concentration of acetic anhydride combined with Compound II was varied from zero moles up to 1.25 moles. The same apparatus was employed as used for the dehydration experiments described in TABLE I wherein 180 g of crude 4'-acetoxyphenylmethylcarbinol (Compound II) was used for each run and phenothiazine (0.1 percent by weight) was used as an inhibitor and mixed with Compound II prior to heating. Also, the catalyst used was 85 weight percent phosphoric acid (0.32 mol %), and the reaction mixture was fed to the heated reaction vessel at a rate of about 2.0 g/min. keeping the residue temperature above 180° C.

TABLE II

| Exp. No. | Compound II (Moles Fed) | Ac₂O (Moles Fed) | Compound I (Moles %) | Compound II (Conv. %) | Compound I Selectivity (%) | Yield (%) | Residue (grams) |
| --- | --- | --- | --- | --- | --- | --- | --- |
| 20 | 0.92 | 0.00 | 0.52 | 99.8 | 57.4 | 57.3 | 64.2 |
| 21 | 0.91 | 0.25 | 0.66 | 98.3 | 73.7 | 72.4 | 41.4 |
| 22 | 0.90 | 0.50 | 0.67 | 95.0 | 78.4 | 74.4 | 38.0 |
| 23 | 0.90 | 0.75 | 0.65 | 95.2 | 76.6 | 72.9 | 36.7 |
| 24 | 0.94 | 1.00 | 0.70 | 94.1 | 78.7 | 74.1 | 29.0 |
| 25 | 0.92 | 1.25 | 0.69 | 93.1 | 80.7 | 75.1 | 32.5 |

The following examples illustrate the effect of the concentration of polymeric residue in the reaction vessel during dehydration of Compound II to yield Compound I.

EXAMPLE 26

Crude 4'-acetoxyphenylmethylcarbinol (Compound II) [0.58 mol] was mixed with acetic anhydride (0.64 mol), phenothiazine (0.1 wt. %) and 85% by weight phosphoric acid (0.32 mol %). This reaction mixture was fed continuous at a rate of about 2.0 g/minute to the hot reaction vessel, as employed in Examples 1–25, and the product was collected overhead through a distillation column. The reaction vessel was immersed in hot oil maintained at 220°–230° C. and the residue temperature was maintained 180°–190° C. The product (155.4 g) containing Compound I was collected overhead through the distillation column and the residue (24.6 g) was accumulated in the hot reaction vessel. 4-Acetoxystyrene (Compound I) was isolated in 74.1% yield.

EXAMPLE 27

To the residue from Example 26, a mixture of crude Compound II (0.58 mol) with acetic anhydride (0.64 mol), phenothiazine (0.1 wt. %) and 85% by weight phosphoric acid (0.32 mol %) was fed continuously as described in Example 26. The product (183.3 g) containing Compound I was collected overhead through the distillation column and the residue was left in the reaction vessel. 4-Acetoxystyrene (Compound I) was isolated in 91.7% yield.

EXAMPLE 28

To the residue from Example 27, a mixture of crude Compound II (0.58 mol) with acetic anhydride (0.64 mol), phenothiazine (0.1 wt. %) and 85% by weight phosphoric acid (0.32 mol %) was fed continuously as described in Example 27. The product (173.6 g) containing Compound I was collected overhead through the distillation column and the residue was left in the reaction vessel along with the residue from Examples 26 and 27. 4-Acetoxystyrene (Compound I) was isolated in 86.7% yield.

The combined 4-acetoxystyrene (Compound I) yield from Examples 26, 27 and 28 was determined to be 84.1%.

We claim:

1. A method for the preparation of 4-acetoxystyrene which comprises heating, in a continuous feed reaction mode or in a semi-continuous feed reaction mode, 4'-acetoxyphenylmethylcarbinol in the presence of a suitable acid anhydride and a suitable dehydration catalyst, wherein said heating is carried out in a manner which subjects said 4'-acetoxyphenylmethylcarbinol to a temperature ranging from about 150° C. to about 300° C. at a pressure ranging from about 5 mm HgA to about 250 mm HgA.

2. The method as defined in claim 1, wherein a suitable polymerization inhibitor is also present with said 4'-acetoxyphenylmethylcarbinol.

3. The method as defined in claim 1, which additionally comprises removing a polymer residue which forms during the preparation of said 4-acetoxystyrene.

4. The method as defined in claim 3, wherein said polymer residue removal is carried out in a manner which maintains the presence of at least some polymer residue, which residue acts as part of the reaction medium for said preparation of 4-acetoxystyrene.

5. The method as defined in claim 4, wherein said polymer residue removal is carried out in a manner which provides a desired steady state quantity of said polymer residue.

6. The method as defined in claim 5, wherein said 4-acetoxystyrene preparation is carried out in a reaction vessel, and wherein said steady state quantity ranges from about 1 volume percent to about 30 volume percent of the volume of said reaction vessel.

7. The method as defined in claim 5, wherein said 4-acetoxystyrene preparation is carried out in a reaction vessel, and wherein the volume of said polymer residue in said reaction vessel ranges between a lower limit of from about 1% to about 29% by volume of said reaction vessel and an upper limit of from about 2% to about 30% by volume of said reaction vessel.

8. The method as defined in claim 1, wherein said heating is conducted at a temperature ranging from about 160° C. to about 300° C., at a vacuum ranging from about 5 mm HgA to about 250 mm HgA.

9. The method as defined in claim 1, wherein said suitable dehydration catalyst is selected from the group consisting of an inorganic bisulfate salt, a mineral acid, an organic acid and any suitable mixture of the foregoing.

10. The method as defined in claim 9, wherein said suitable dehydration catalyst is selected from ammonium bisulfate, potassium bisulfate, phosphorous acid, phosphoric acid, p-toluenesulfonic acid and any suitable mixture of the foregoing.

11. A method for preparing 4-acetoxystyrene in a continuous feed reaction mode which comprises the steps of:
 a) feeding, in a continuous manner, a reaction mixture comprising 4'-acetoxyphenylmethylcarbinol, a suitable acid anhydride and a suitable dehydration catalyst, into a reaction vessel, which vessel is heated in a manner which subjects said mixture to a temperature ranging from about 150° C. to about 300° C. at a pressure ranging from about 5 mm HgA to about 250 mm HgA whereby said mixture produces 4-acetoxystyrene, a co-product, and a polymer residue;
 b) removing at least a portion of said 4-acetoxystyrene and at least a portion of said co-product, as they are produced, from said reaction vessel; and c) removing periodically or continuously at least a portion of said polymer residue from said reaction vessel.

12. The method as defined in claim 11, wherein said reaction mixture additionally comprises a suitable polymerization inhibitor.

13. The method as defined in claim 11, wherein the amount of said polymer residue removed from said reaction vessel is such that a volume of polymer residue ranging from about 1 to about 30 percent of the volume of said reaction vessel is maintained in said reaction vessel.

14. The method as defined in claim 13, wherein said volume of polymer residue ranges from about 5 to about 15 percent of the volume of said reaction vessel.

15. The method as defined in claim 11, wherein said heating is conducted at a temperature ranging from about 160° C. to about 300° C., at a vacuum ranging from about 5 mm HgA to about 250 mm HgA.

16. The method as defined in claim 11, wherein said suitable dehydration catalyst is selected from the group consisting of an inorganic bisulfate salt, a mineral acid, an organic acid and any suitable mixture of the foregoing.

17. The method as defined in claim 16, wherein said suitable dehydration catalyst is selected from the group consisting of ammonium bisulfate, potassium bisulfate, phosphorous acid, phosphoric acid, p-toluenesulfonic acid and any suitable mixture of the foregoing.

18. A method for the preparation of 4-acetoxystyrene comprising the steps of:
   a) introducing into a reaction vessel a reaction mixture comprising 4'-acetoxyphenylmethylcarbinol, a suitable acid anhydride, and a suitable dehydration catalyst;
   b) heating said reaction mixture in a manner which subjects said mixture to a temperature ranging from about 150° C. to about 300° C. at a pressure ranging from about 5 mm HgA to about 250 mm HgA, whereby said mixture produces 4-acetoxystyrene, a co-product and a polymer residue; and
   c) removing from said reaction vessel at least a portion of said co-product as it is formed.

19. The method as defined in claim 18, wherein at least a portion of said 4-acetoxystyrene is removed from said reaction vessel as it is formed.

20. The method as defined in claim 18 or claim 19, wherein said reaction mixture additionally comprises a suitable polymerization inhibitor.

21. The method as defined in claim 18 or claim 19, which further comprises removing at least a portion of said polymer residue during said preparation of said 4-acetoxystyrene.

22. The method as defined in claim 21, wherein said removal of said portion of polymer residue is made periodically.

23. The method as defined in claim 21, wherein said removal of said portion of polymer residue is made in a manner which provides a desired quantity of said polymer residue in said reaction vessel during at least a substantial portion of the time during which 4-acetoxystyrene is produced.

24. The method as defined in claim 23, wherein said desired quantity of polymer residue ranges in volume from about 1 percent to about 30 percent of the volume of said reaction vessel.

25. The method as defined in claim 24, wherein said desired quantity of polymer residue ranges in volume from about 5 percent to about 15 percent of the volume of said reaction vessel.

26. The method as defined in claim 18 or claim 19, wherein said heating is conducted at a temperature ranging from about 160° C. to about 300° C., at a vacuum ranging from about 5 mm HgA to about 150 mm HgA.

27. The method as defined in claim 18 or claim 19, wherein said suitable dehydration catalyst is selected from the group consisting of an inorganic bisulfate salt, a mineral acid, an organic acid and any suitable mixture of the foregoing.

28. The method as defined in claim 27, wherein said suitable dehydration catalyst is selected from the group consisting of ammonium bisulfate, potassium bisulfate, phosphorous acid, phosphoric acid, p-toluene sulfonic acid and any suitable mixture of the foregoing.

29. The method as defined in claim 21, wherein said reaction mixture is introduced into said reaction vessel in a semi-continuous feed mode.

30. The method as defined in claim 29, wherein said polymer residue is removed continuously.

31. The method as defined in claim 29, wherein said polymer residue is removed periodically.

32. In a method for the preparation of 4-acetoxystyrene in a semi-continuous feed reaction mode, wherein the improvement comprises the steps of:
   a) feeding in a continuous manner a reaction mixture comprising 4'-acetoxyphenylmethylcarbinol, a suitable acid anhydride, and a suitable dehydration catalyst into a reaction vessel which is maintained at a temperature suitable to subject said reaction mixture to a temperature ranging from about 150° C. to about 300° C. at a pressure ranging from about 5 mm HgA to about 250 mm HgA, whereby said mixture produces 4-acetoxystyrene, a co-product and a polymer residue;
   b) removing at least a portion of said 4-acetoxystyrene and at least a portion of said co-product, as they are formed, from said reaction vessel;
   c) interrupting said feeding of said reaction mixture while continuing said removing of said 4-acetoxystyrene and co-product for a period of time sufficient to reduce the amount of said 4-acetoxystyrene and said co-product remaining in said reaction vessel to an insignificant level, whereby process economics are satisfied;
   d) subsequent to said interruption of said feeding and subsequent to said reduction of said 4-acetoxystyrene and said co-product to said insignificant amount, removing at least a portion of said polymer residue from said reaction vessel; and
   e) repeating steps a) through c) at least once, wherein step d) is repeated prior to each repetition of step a).

* * * * *